United States Patent [19]
Branner et al.

[11] Patent Number: 5,482,849
[45] Date of Patent: Jan. 9, 1996

[54] SUBTILISIN MUTANTS

[75] Inventors: Sven Branner, Lyngby; Sven Hastrup, Copenhagen; Nina Eriksen, Frerderiksberg; Poul Lindegaard, Copenhagen; Ole H. Olsen, Broenshoej, all of Denmark; Eric Casteleijn, Capelle, Netherlands; Maarten R. Egmond, Linschoten, Netherlands; Johan Haverkamp, Bergschenhoek, Netherlands; Wouter Musters, Maassluis, Netherlands; Jakob de Vlieg, Rotterdam, Netherlands

[73] Assignee: Novo Nordisk A/S, Bagsvaerd, Denmark

[21] Appl. No.: 811,502

[22] Filed: Dec. 20, 1991

[30] Foreign Application Priority Data

Dec. 21, 1990 [EP] European Pat. Off. .............. 90610077
Dec. 21, 1990 [GB] United Kingdom ................... 9027836

[51] Int. Cl.$^6$ .............................. C12N 9/54; C12N 9/56; C12N 9/50; C12N 15/57
[52] U.S. Cl. .................. 435/222; 435/221; 435/220; 435/172.3; 435/252.31; 435/320.1; 536/23.2; 935/10; 935/14; 935/29; 935/66
[58] Field of Search ..................... 435/222, 221, 435/220, 219, 69.1, 172.3, 25.31, 183; 536/27, 23.2

[56] References Cited

U.S. PATENT DOCUMENTS

| | | | |
|---|---|---|---|
| 4,980,288 | 4/1990 | Bryan et al. | 435/222 |
| 4,990,452 | 2/1991 | Bryan et al. | 435/222 |
| 5,013,657 | 5/1991 | Bryan et al. | 435/172.3 |
| 5,155,033 | 10/1992 | Estell et al. | 435/221 |
| 5,182,204 | 1/1993 | Estell et al. | 435/222 |
| 5,185,258 | 2/1993 | Caldwell et al. | 435/220 |
| 5,208,158 | 5/1993 | Bech et al. | 435/219 |
| 5,217,878 | 6/1993 | Van Eckelen et al. | 435/69.1 |
| 5,260,207 | 11/1993 | Pantoliano et al. | 435/221 |
| 5,264,366 | 11/1993 | Ferrari et al. | 435/252.31 |
| 5,336,611 | 8/1994 | Van Eckelen et al. | 435/221 |

FOREIGN PATENT DOCUMENTS

| | | |
|---|---|---|
| 0130756 | 1/1985 | European Pat. Off. . |
| 0214435 | 7/1986 | European Pat. Off. . |
| 0251446 | 1/1988 | European Pat. Off. . |
| 0260105 | 3/1988 | European Pat. Off. . |
| 0405901 | 1/1991 | European Pat. Off. . |
| 0405902 | 1/1991 | European Pat. Off. . |
| 0415296 | 3/1991 | European Pat. Off. . |
| WO87/04461 | 7/1987 | WIPO . |
| WO87/05050 | 8/1987 | WIPO . |
| WO89/06279 | 7/1989 | WIPO . |
| WO91/00345 | 1/1991 | WIPO . |
| WO91/00334 | 1/1991 | WIPO . |

OTHER PUBLICATIONS

Thomas et al., Nature, vol. 318, pp. 375–376 (1985).
Russell et al., J. Mol. Biol., vol. 193, pp. 803–813 (1987).
Russell et al., Nature, vol. 328, pp. 496–500 (1987).
White et al., Principles of Biochem., pp. 271–272 (1973).
Fergus G. Priest, Bacteriological Reviews, vol. 41, pp. 711–753 (1977).
Vasantha et al., J. Bacteriol., vol. 159, No. 3, pp. 811–819 (1984).
Jacobs et al., Nucl. Acids vol. 13, No. 24, pp. 8913–8926 (1985).
Nedkov et al., Biol. Chem. Hoppe–Seyler, vol. 366, pp. 421–430 (1985).
Svendsen et al., FEBS Lett., vol. 196, No. 2, pp. 228–232 (1986).
Meloun et al., FEBS Lett., vol. 183, No. 2, pp. 195–200 (1985).
Jany et al., Biol. Chem. Hoppe–Seyler, vol. 366, pp. 485–492 (1985).
Joseph Kraut, Ann. Rev. Biochem., vol. 46, pp. 331–358 (1977).
Wells et al., Proc. Natl. Acad. Sci. USA, vol. 84, pp. 1219–1223 (1987).
Kurihara et al., J. Biol. Chem., vol. 247, No. 17, pp. 5619–5631 (1972).
Wells et al., Phil. Trans. R. Soc. Lond. A 317, pp. 123–131 (1986).
Hwang et al., Biochemistry, vol. 26, pp. 2669–2673 (1987).
Rao et al., Nature, vol. 328, pp. 551–553 (1987).
Stahl and Ferrari, J. Bacteriology, vol. 158, No. 2, pp. 411–418 (1984).
Bott, R., The Journal of Biological Chemistry 263(16): 7895–7906, 1988.
Wells, J. A., et al., Proceedings of the National Academy of Sciences, U.S.A., 84: 5167–5171, 1987.
Cunningham, B. C., et al., Protein Engineering, 1(4): 319–325, 1987.
Muraki, M., et al., Protein Engineering, 2(1): 49–54, 1988.
Fersht, A. R., et al., Protein Engineering, 2(7): 527–530, 1989.
Pähler, A., et al., The EMBO Journal, 3(6): 1311–1314, 1984.

*Primary Examiner*—Robert A. Wax
*Assistant Examiner*—William W. Moore
*Attorney, Agent, or Firm*—Steve T. Zelson; Elias J. Lambiris

[57] ABSTRACT

This invention relates to enzymes, to rDNA techniques applicable for example to their production, to mutated genes, vectors and mutant and transformed microorganisms useful in their production, and to their uses including for example enzymatic detergent and cleaning compositions containing them.

45 Claims, No Drawings

SUBTILISIN MUTANTS

FIELD OF THE INVENTION

This invention relates to enzymes, to rDNA techniques applicable for example to their production, to mutated genes, vectors and mutant and transformed microorganisms useful in their production, and to their uses including for example enzymatic detergent and cleaning compositions containing them.

In particular embodiments the invention relates to modified enzymes and their manufacture and use, especially modified proteases. Such modified proteases include those derived from microorganisms descended from an ancestor which has been modified genetically, e.g. by rDNA technique.

In particular embodiments the invention relates to the preparation and use of modified enzymes, especially modified alkaline serine proteases, especially those of bacterial and fungal origin. Thus the invention as described below provides inter alia techniques for production of protease, e.g. Bacillus subtilis protease and other subtilisin proteases, and further provides genetically modified forms of such proteases, and the use of such enzymes in detergent and cleaning compositions.

BACKGROUND OF THE INVENTION

Enzymes and especially proteases have for more than 20 years been used in detergent and cleaning compositions for removing or facilitating the removal of unwanted proteinaceous soil, etc. Commercially most important among the enzymes used for these purposes are proteases, especially subtilisin proteases.

Although proteases have been used in the detergent industry for more than 20 years, it is still not exactly known which physical or chemical characteristics are responsible for good washing results. The currently used proteases have been found by isolating proteases from nature and testing them in detergent formulations.

Serine proteases are known as a class of enzymes, including subtilisins, which catalyse the hydrolysis of peptide bonds, and which are characterised by an essential serine residue at the active site (White, Handler and Smith, "Principles of Biochemistry", 5th edition, McGraw-Hill Book Co, New York, 1973, pp 271–272).

The known serine proteases have molecular weights in the 25,000 to 30,000 range. They are inhibited by diisopropyl-fluorophosphonate, but in contrast to metalloproteases, are resistant to ethylenediamine-tetra-acetic acid (EDTA) (although they are stabilised at high temperatures by calcium ion). They hydrolyse simple terminal esters and are similar in activity to eukaryotic chymotrypsin, also a serine protease. The alternative term, alkaline protease, reflects the high pH optimum of the serine proteases, from pH 9.0 to 11.0 (for review, see Priest, 1977, Bacteriological Rev. 41:711–753).

A subtilisin is a serine protease produced by Gram-positive bacteria or fungi. A wide variety of subtilisins have been identified, and the amino acid sequences of at least eight subtilisins have been determined. These include six subtilisins from Bacillus strains, namely, subtilisin 168, subtilisin BPN', subtilisin Carlsberg, subtilisin DY, subtilisin amylosacchariticus, and mesentericopeptidase (Kurihara et al., 1972, J. Biol. Chem. 247:5629–5631; Stahl and Ferrari, 1984, J. Bacteriol. 159:811–819, Jacobs et al., 1985, Nucl. Acids. Res. 13:8913–8926; Nedkov et al., 1985, Biol. Chem. Hoppe-Seyler 366:421–430, Svendsen et al., 1986, FEBS Lett. 196:228–232), and two fungal subtilisins, subtilisin thermitase from Thermoactinomyces vulgaris (Meloun et al., 1985, FEBS Lett. 1983:195–200) and proteinase K from Tritirachium album (Jany and Mayer, 1985, Biol. Chem. Hoppe-Seyler 366:584–492).

Subtilisins are well-characterized physically and chemically. In addition to knowledge of the primary structure (amino acid sequence) of these enzymes, over 50 high resolution X-ray structures of subtilisin have been determined which delineate the binding of substrate, transition state, products, three different protease inhibitors, and define the structural consequences for natural variation (Kraut, 1977, Ann. Rev. Biochem. 46:331–358).

Random and site-directed mutations of the subtilisin gene have both arisen from knowledge of the physical and chemical properties of the enzyme and contributed information relating to subtilisin's catalytic activity, substrate specificity, tertiary structure, etc. (Wells et al., 1987, Proc. Natl. Acad. Sci. U.S.A. 84; 1219–1223; Wells et al., 1986, Phil. Trans. R. Soc. Lond. A. 317:415–423: Hwang and Warshel, 1987, Biochem. 26:2669–2673; Rao et al., 1987, Nature 328:551-554).

The technique of site-directed mutagenesis of the subtilisin gene has attracted much attention, and various mutations are described in the following patent applications and patents:

EP 0 130 756 (Genentech) (corresponds to U.S. Pat. No. 4,760,025 (Genencor)) relates to site specific or randomly generated mutations in "carbonyl hydrolases" and subsequent screening of the mutated enzymes for various properties, such as Kcat/Km ratio, pH-activity profile, and oxidation stability. Apart from revealing that site-specific mutation is feasible, and that mutation of subtilisin BPN' in certain specified positions, i.e. -1Tyr, 32Asp, 135Asn, 104Tyr, 222Met, 166Gly, 64His, 169Gly, 189Phe, 33Ser, 221Ser, 217Tyr, 156Glu or 152Ala, provide for enzymes exhibiting altered properties, this application does not contribute to solving the problem of deciding where to introduce mutations in order to obtain enzymes with desired properties.

EP 0 214 435 (Henkel) relates to cloning and expression of subtilisin Carlsberg and two mutants thereof (but gives no reason to mutate 158Asp to 158Ser and 161Ser to 161Asp).

International Patent Application WO 87/04461 (Amgen) describes reducing the number of Asn-Gly sequences present in the parent enzyme to obtain mutated enzymes exhibiting improved pH and heat stabilities, with emphasis on removing, mutating, or modifying the 109Asn and the 218Asn residues in subtilisin BPN'.

International Patent Application WO 87/05050 (Genex) discloses random mutation and subsequent screening of a large number of mutants of subtilisin BPN' for improved properties, and describes mutations in positions 218Asn, 131Gly, 254Thr, 166Gly, 116Ala, 188Ser, 126Leu, and 53Ser.

EP 0 251 446 (Genentech) describes how homology considerations at both primary and tertiary structural levels may be applied to identify equivalent amino acid residues whether conserved or not. This information together with the authors' knowledge of the tertiary structure of subtilisin BPN' led the authors to select a number of positions susceptible to mutation with an expectation of obtaining mutants with altered properties. The positions so identified are: 124Met, 222Met, 104Tyr, 152Ala, 156Glu, 166Gly, 169Gly, 189Phe, 217Tyr. Also 155Asn, 21Tyr, 22Thr, 24Ser, 32Asp, 33Ser, 36Asp, 46Gly, 48Ala, 49Ser, 50Met, 77Asn, 87Ser, 94Lys, 95Val, 96Leu, 107Ile, 110Gly, 170Lys, 171Tyr, 172Pro, 197Asp, 199Met, 204Ser, 213Lys, and 221Ser are identified as having influence on various properties of the enzyme, and a number of mutations are exemplified to support these suggestions. In addition to single mutations in these positions the authors also performed a number of multiple mutations. Further the authors identify 215Gly, 67His, 126Leu, 135Leu, and amino acid residues within the segments 97–103, 126–129, 213–215, and 152–172 as having interest, but mutations in these positions are not exemplified.

EP 0 260 105 (Genencor) describes modification of certain properties in enzymes containing a catalytic triad by selecting an amino acid residue within about 15 A from the catalytic triad and replace the selected amino acid residue with another residue. Enzymes of the subtilisin type described in the present specification are specifically mentioned as belonging to the class of enzymes containing a catalytic triad. In subtilisins positions 222 and 217 are indicated as preferred positions for replacement.

Also, it has been shown by Thomas, Russell, and Fersht (Nature (1985) 318, 375–376) that changing 99Asp into 99Ser in subtilisin BPN' changes the pH dependency of the 803–813) the same authors also discuss the substitution of 156Ser in place of 156Glu. Both these mutations are within a distance of about 15 A from the active 64His.

In Nature 328, 496–500 (1987) Russell and Fersht discuss the results of their experiments and present rules for changing pH-activity profiles by mutating an enzyme to obtain changes in surface charge.

At present the following subtilisin proteases are well-known and many of them are marketed in large quantities in many countries of the world, especially for detergent uses:
Subtilisin BPN' or Novo, available from e.g. Sigma, St Louis, USA;
Subtilisin Carlsberg, marketed by Novo Nordisk A/S (Denmark) as ALCALASE (TM) and by IBIS (Holland) as MAXATASE (TM);
A Bacillus lentus subtilisin, marketed by Novo Nordisk A/S (Denmark) as SAVINASE (TM);
SAVINASE (TM) analogues, such as MAXACAL (TM) marketed by IBIS and OPTICLEAN (TM) marketed by Miles Kali Chemie (Germany);
A Bacillus lentus subtilisin, marketed by Novo Nordisk A/S (Denmark) as ESPERASE (TM);
KAZUSASE (TM) marketed by Showa Denko (Japan).

To be effective, however, such enzymes must not only exhibit activity under washing conditions, but must also be compatible with other detergent components during production and storage.

For example, subtilisins may be used in combination with other enzymes active against other substrates, and the selected subtilisin should possess stability towards such enzymes, and also the selected subtilisin preferably should not digest the other enzymes. Also, the chosen subtilisin should be resistant to the action from other components in the detergent formulation, such as bleaching agents, oxidising agents, etc., in particular an enzyme to be used in a detergent formulation should be stable with respect to the oxidizing power, calcium binding properties, detergency, and pH conditions rendered by the non-enzymatic components in the detergent during storage and in the wash liquor during wash. The ability of the enzyme to remain stable in the wash liquor is often referred to as its washing ability or washability.

Naturally occurring subtilisins have been found to possess properties which are highly variable in relation to their washing power or ability under variations in parameters such as pH and ionic strength. Several of the above marketed detergent proteases, indeed, have a better performance than those marketed about 20 years ago, but for optimal performance each enzyme has its own specific conditions regarding formulation and wash conditions, e.g. pH, temperature, ionic strength (I), active system, builders, etc.

As a consequence it is found that an enzyme possessing desirable properties at low pH and low I may be less attractive at more alkaline conditions or vice versa.

Furthermore, it is desirable to produce and use enzymes which are relatively resistant to changes in pH of wash liquors which occur during washing processes.

It is possible now to construct enzymes having desired amino acid sequences, and as indicated above a fair amount of research has been devoted to designing subtilisins with altered properties. Among the proposals, the technique of producing and screening a large number of mutated enzymes as described in EP 0 130 756 (Genentech) (US Pat. No. 4,760,025 (Genencor)) and International patent application WO 87/05050 (Genex) corresponds to the classical method of isolating native enzymes and screening them for their properties, but is more efficient.

Since a subtilisin protease typically comprises about 275 amino acid residues each capable of being 1 out of 20 possible naturally occurring amino acids, one very serious drawback in that procedure is the very large number of mutations generated that has to be submitted to a preliminary screening prior to further testing of selected mutants showing interesting characteristics at the first screening, since no guidance is indicated in determining which amino acid residues to mutate in order to obtain a desired enzyme with improved properties for the use in question, such as, in this case formulating detergent compositions exhibiting improved washing ability under specified conditions of the wash liquor.

A procedure as outlined in these patent applications will consequently only be slightly better than the traditional random mutation procedures which have been known for years.

The other known techniques relates to changing specific properties, such as hydrolysis rate (EP 0 260 105 (Genencor)) and pH-activity profile (Thomas, Russell, and Fersht, supra). None of these publications relates to changing the wash performance or 'washability' of enzymes.

Indeed, no relationship has yet been identified in the art between such well defined properties of an enzyme and the wash performance or 'washability' of an enzyme.

In International Patent Application No. WO 89/06279 (PCT/DK 88/00002) (Novo Industri A/S) it is proposed to use the concept of homology comparison to determine which amino acids should be changed and which amino acids should be introduced in order to obtain a desired change in washability.

(Unpublished) European patent application 90306952.4 (Unilever) describes the production and use of mutant subtilisin proteases with altered pI, and detergent compositions containing them.

A remaining problem seems to be that although much research has been directed at revealing the mechanism of protease enzyme action, still only little is known about the factors in structure and amino acid residue combinations that determine the properties of enzymes in relation to their wash performance.

Consequently there still exists a need for further improvement and tailoring of protease enzymes to wash systems, as well as a better understanding of the mechanism of protease action in the practical use of cleaning or detergent compositions.

DESCRIPTION OF THE INVENTION

In the context of this invention, a mutant protease, e.g. a mutant subtilisin protease, means a protease that has been produced by an organism which is expressing a mutant gene derived from a parent microorganism which possessed an original or parent gene and which produced a corresponding parent enzyme, the parent gene having been mutated in order to produce the mutant gene from which said mutant protease is produced when expressed in a suitable host.

As noted above, proteases of bacterial and fungal origin, especially subtilisin proteases, have shown themselves to be useful inter alia in detergent and cleaning compositions, such as for example laundry detergents.

Subtilisins and other alkaline proteases tolerate alkaline washing conditions to a certain extent that has allowed their use in practice. Nevertheless, they show a certain dependence of activity and stability on pH in the alkaline range, and it is desirable to provide enzyme preparations of which the properties are more tractable at alkaline pH than the properties of the enzymes available up to now.

The invention in one of its aspects provides protease produced by rDNA technique, e.g. a subtilisin protease, which carries at least one mutation of its amino acid sequence resulting in a lower degree of variation, compared with the parent protease, of the molecular charge of the protease over a pH range (e.g. approaching substantial constancy of charge over a pH range, e.g. approaching neutrality).

Also provided by the invention are enzymatic detergent compositions comprising, besides (for example) detergent surfactant and detergent adjuncts, protease produced by rDNA technique, which carries at least one mutation of its amino acid sequence resulting in a lower degree of variation, compared with the parent protease, of the molecular charge of the protease over a pH range (e.g. approaching substantial constancy of charge over a pH range, e.g. approaching neutrality).

According to the invention, such a lower degree of variation in molecular charge, especially for example a substantial neutrality or constancy of molecular charge over a pH range, provides increased flexibility of detergent formulation constraints, and can allow formulation of detergents with pH closer in several cases to a desired pH. Such enzymes can also show less sensitivity than wild-type enzymes to changes of pH during use.

Such a mutant enzyme can bring advantage in activity, stability, and/or wash performance, and/or the capacity to be used over a broader pH range, when used as part of a detergent or cleaning composition.

Such a mutant enzyme can also reduce undesirable performance changes during a laundry wash cycle by showing less sensitivity to changes of pH in the wash liquor.

Such an enzyme can be applied with substantially equivalent performance in detergents of relatively high and relatively low pH.

One of the widely used subtilisin proteases (subtilisin 309, referred to above) shows a sensitivity to pH reflected in a change of net molecular charge of about 8 units per molecule over the pH range 7 to 11, from about +5 at the lower pH to about −3 at the higher pH.

Useful examples of mutant protease enzymes involved in the present invention can show a lower degree of variation, e.g. a substantially reduced change of molecular charge, with pH compared with such a wild-type enzyme, even approaching substantial constancy and in certain cases neutrality of molecular charge, e.g. a change of not more than 5 charge units per molecule, e.g. not more than 3 charge units per molecule, or a lesser change, in some cases not more than about 1 charge unit per molecule, over a pH range which may be more or less extended, e.g. the pH range from about 8 to about 11, optionally the wider range from about 7 to about 11.

Most usually the charge becomes more negative with increasing pH. It can be sufficient if the mutant protease shows a correspondingly reduced rate of change of molecular charge with pH, but over a pH range which is less extended than the range 7 to 11, e.g. over a pH range of at least 0.5 pH unit, e.g. at least 1 pH unit, e.g. at least 2 or 3 pH units, such less extended range being located within the pH range from about 7 to about 11, e.g. within the range about 8 to about 11.

The molecular charge at pH values within the region of reduced variability of charge with pH can be within the range +5 to −3 charge units per molecule, e.g. within the range + to −1 units, sometimes a net charge within the range ±1, e.g. ±0.5), e.g. close to zero or slightly positive.

In some cases, the net charge of the protease can for example remain almost constant or almost zero within a range of variation of ±1, or more narrowly ±0.5 charge per molecule.

Mutant enzymes according to embodiments of this invention can be made by application of the generally known rDNA techniques exemplified for example in the publications cited above and references cited therein (incorporated herein by reference).

The embodiments of mutant enzymes according to the invention mentioned below are identified by reference to the following abbreviations for each of the amino acids of natural occurrence in proteins:

A=Ala=Alanine
V=Val=Valine
L=Leu=Leucine
I=Ile=Isoleucine
P=Pro=Proline
F=Phe=Phenylalanine
W=Trp=Tryptophan
M=Met=Methionine
G=Gly=Glycine
S=Ser=Serine
T=Thr=Threonine
C=Cys=Cysteine
Y=Tyr=Tyrosine
N=Asn=Asparagine
Q=Gln=Glutamine
D=Asp=Aspartic acid
E=Glu=Glutamic acid
K=Lys=Lysine
R=Arg=Arginine
H=His=Histidine
B=Asx=Asp or Asn
Z=Glx=Glu or Gln References herein to numbered amino acid sequence positions which are the subject of mutations o be made in accordance with this invention, are references to amino acid residues and their number as they occur in the sequence of subtilisin BPN'. The invention also includes modified variants of other subtilisin proteases, e.g. those whose sequence is given in Table I in International Patent Publication No. WO 91/00345, which is hereby incorporated by reference. In order to apply the numbered mutation sites referred to herein to such other proteases, the numerical part of the reference is to be understood as a reference to the corresponding position of such another homologous subtilisin protease in the sense of its maximum homology with subtilisin BPN'. Such a corresponding position may differ in number along the chain of the other protease by reason of apparent deletion(s) or insertion(s) in the gene of such other protease by comparison with that of the gene of BPN'. A deletion or absent amino acid is indicated in said table by '*', and an insertion relative to BPN' by a lower case alphabetical suffix on the position number.

According to the invention it is preferred that the mutant subtilisin enzyme represents a mutation of a parent enzyme selected from subtilisin BPN', subtilisin amylosachariticus, subtilisin 168, subtilisin mesentericopeptidase, subtilisin Carlsberg, subtilisin DY, subtilisin 309, subtilisin 147, thermitase, Bacillus PB92 protease, and proteinase K, preferably subtilisin 309, subtilisin 147, subtilisin Carlsberg, aqualysin, or Bacillus PB92 protease.

Among the useful mutant subtilisin proteases within the scope of this invention are mutant enzymes carrying mutations of lysine, histidine, cysteine and/or tyrosine residues (which often titrate or have pKa values within the range 8–11) to replace them by non-titrating residues or residues (especially residues other than tyrosine) which have pKa outside that range, or optionally also outside the range 7–12, especially e.g. lysine or cysteine to arginine, leucine, threonine, asparagine, glutamate or aspartate; tyrosine to phenylalanine, threonine, valine, tryptophan or glutamate; histidine to glutamine, asparagine, serine, glutamate or aspartate.

In particular embodiments of the invention any of the following mutations or sets of mutations can be introduced at the sites indicated:

H17Q, K27R, H39S, E54D, Y91F, K94R, H120D, H120N, Y167E, Y167F, Y171V, Y192E, Y192F, Y209F, Y214T, H226S, K235L, K235R, K237R, K251E, K251N, Y263F.

The mutations E54D and K94R should normally be introduced together.

These examples of mutations can be further grouped as follows:

a—K27R;
b—H17Q+K27R+H39S;
c—E54D+Y91F+K94R;
d—E54D+Y91F+K94R+H120D;
e—E54D+Y91F+K94R+H120N;
f—Y167F+Y171V+Y192F+Y209F+Y214T;
g—K235L+K237R+K251E+Y263F;
h—K235L+K237R+K251N+Y263F;
i—H226S+K235L+K237R+K251N+Y263F;
k—H226S+K235L+K237R+K251E+Y263F;
g'—K235R+K237R+K251E+Y263F;
h'—K235R+K237R+K251N+Y263F;
i'—H226S+K235R+K237R+K251N+Y263F;
k'—H226S+K235R+K237R+K251E+Y263F;

Accordingly, embodiments of the invention also include for example mutants possessing the sets of mutations corresponding to a+c+f+g, b+d+f+i, b+e+f+k, b+e+f+i, b+d+f+k, a+c+f+g', b+d+f+i', b+e+f+k', b+e+f+i', b+d+f+k', where the letters denote the mutations or sets of mutations indicated in the preceding paragraph.

Particular examples of mutant proteases of interest are mutants as follows:
A: K27R;
B: K235R+K237R+K251E+Y263F;
C: E54D+Y91F+K94R;
D: K27R+E54D+Y91F+K94R+Y209F+Y214T+K235R+ K237R+K251 E+Y 236F;
E: K27R+E54D+Y91F+K94R+Y167F+Y171V+Y192F+ Y209F+Y214T+K235R+K237R+K251E+Y263F (all Y, K changed);
F: as mutant E with two further mutations adding the charge of a D residue and one adding the charge of an E residue
G: as mutant F with further mutation of histidines at positions 17, 39, 120, 226 to neutral residues
H: as mutant G with the N-terminal chemically modified (blocked) to give a neutral group or a group having a $pK_a$ outside the range from 7 to 12.

As mentioned in connection with protease H above, and as applicable generally, it can also be useful to modify the N-terminal amino-group of the protease (often having a $pK_a$ of about 8 in a polypeptide molecular environment), by treatment with a modifying reagent e.g. to achieve acylation or alkylation of the protease after its production by the producer microorganism, in order to contribute a degree of stabilisation of the charge at alkaline pH in the range 8–11, e.g. by arranging that the result of the blocking treatment replaces the N-terminal amino-group with a group having pKa outside the range about 8–11, e.g. outside the range about 7–12.

Suitable methods are disclosed for example in 'Chemical Modification of Proteins', G. E. Means, R. E. Feeney, 1971 Holden Day Inc, San Francisco, and 'In Vivo Chemical Modification of Proteins' by Finn Wold, Ann Rev Biochem 50 (1981), 783–814. The most suitable methods include processes (i) to modify the terminal amino-group, leaving a positively charged group of higher pK, e.g. by reaction with ethyl acetimidate to convert the amino group to a homoguanidinium group, or by guanidination with O-methyl isourea; (ii) to neutralise the N-terminal e.g. by acetylation with acetic anhydride or carbamylation with cyanate; or (iii) to convert the terminal amino-group to a negatively charged group e.g. by acylation with succinic anhydride. These methods also affect accessible lysine residues.

The present invention also comprises the use of the mutant enzymes of the invention in cleaning and detergent compositions, and extends also to cleaning and detergent compositions comprising such mutant enzymes.

These enzymes can be used in well-known standard amounts in detergent compositions. The amounts may range very widely, e.g. about 0.0002–0.01, e.g. about 0.005–0.05, Anson units per gram of the detergent composition. Expressed in other units, the protease can be included in the compositions in amounts in the order of from about 0.1 to 100 GU/mg (e.g. 1–50, especially 5–20 GU/mg) of the detergent formulation, or any amount in a wide range centering at about 0.01–4, e.g. 0.1–0.4 kNPU per g detergent formulation.

A KNPU is defined as in technical documentation published by Novo Nordisk A/S.

A GU is a Glycine Unit, defined as the proteolytic enzyme activity which, under standard conditions, during a 15-minute incubation at 40 deg C, with N-acetyl casein as substrate, produces an amount of NH2-group equivalent to 1 micromole of glycine.

It can for example be suitable to use the present enzymes at the rate of about 0.25 mg enzyme protein per liter of wash liquor, corresponding to an enzyme activity of the order of 0.08 kNPU per liter. Corresponding detergent formulations can contain the enzymes in for example an amount of the order of 0.1–0.4 kNPU/g.

Such compositions comprise in addition to any one or more of the mutant subtilisin enzymes in accordance to any of the preceding aspects of the invention alone or in combination any of the usual components included in such compositions which are well-known to the person skilled in the art.

Such components comprise builders, such as phosphate or zeolite builders, surfactants, such anionic, cationic or nonionic surfactants, polymers, such as acrylic or equivalent polymers, bleach systems, such as perborate- or amino-containing bleach precursors or activators, structurants, such as silicate structurants, alkali or acid to adjust pH, humectants, and or neutral inorganic salts.

The detergent compositions can also contain further enzymes.

For example, lipase can usefully be added in the form of a granular composition, (alternatively a solution or a slurry), of lipolytic enzyme with carrier material (e.g. as in EP 258068 (Novo Nordisk A/S) and the Lipolase and other enzyme compositions of Novo Nordisk A/S).

The added amount of lipase can be chosen within wide limits, for example 50 to 30,000 LU/g per gram of the surfactant system or of the detergent composition, e.g. often at least 100 LU/g, very usefully at least 500 LU/g, sometimes preferably above 1000, above 2000 LU/g or above 4000 LU/g or more, thus very often within the range 50–4000 LU/g and possibly within the range 200–1000 LU/g. In this specification lipase units are defined as they are in EP 258068.

The lipolytic enzyme can be chosen from among a wide range of lipases: in particular the lipases described in for example the following patent specifications, EP 214761 (Novo Nordisk A/S), EP 0 258 068 and especially lipases showing immunological cross-reactivity with antisera raised against lipase from Thermomyces lanuginosus ATCC 22070, EP 0 205 208 and EP 0 206 390 and especially lipases showing immunological cross-reactivity with antisera raised against lipase from Chromobacter viscosum var lipolyticum NRRL B-3673, or against lipase from Alcaligenes PL-679, ATCC 31371 and FERM-P 3783, also the lipases described in specifications WO 87/00859 (Gist-Brocades) and EP 0 204 284 (Sapporo Breweries). Suitable in particular are for example the following commercially available lipase preparations: Novo Lipolase, Amano lipases CE, P, B, AP, M-AP, AML, and CES, and Meito lipases MY-30, OF, and PL, also Esterase MM, Lipozym, SP225, SP285, Saiken lipase, Enzeco lipase, Toyo Jozo lipase and Diosynth lipase (Trademarks).

Genetic engineering of these further lipase enzymes can be achieved by extraction of an appropriate lipase gene, e.g. the gene for lipase from Thermomyces lanuginosus or from a mutant thereof, and introduction and expression of the gene or derivative thereof in a suitable producer organism such as an Aspergillus. The techniques described in WO 88/02775 (Novo Nordisk A/S), EP 0 243 338 (Labofina), EP 0 268 452 (Genencor) and notably EP 0 305 216 (Novo Nordisk A/S) or EP 0 283 075 (Gist-Brocades) may be applied and adapted.

Similar considerations apply mutatis mutandis in the case of other enzymes, which may also be present. Without limitation: Amylase can for example be used when desired, in an amount in the range about 1 to about 100 MU (maltose units) per gram of detergent composition, (or 0.014–1.4, e.g. 0.07–0.7, KNU/g (Novo units)). Cellulase can for example be used when desired, in an amount in the range about 0.3 to about 35 CEVU units per gram of the detergent composition.

Among the usual detergent ingredients which may be present in usual amounts in the detergent compositions of this invention, are the following: The compositions may be built or unbuilt, and may be of the zero-P type (i.e. not containing any phosphorus-containing builders). Thus the composition may contain in aggregate for example from 1–50%, e.g. at least about 5% and often up to about 35–40% by weight, of one or more organic and/or inorganic builders. Typical examples of builders include those already mentioned above, and more broadly include alkali metal ortho, pyro, and tripolyphosphates, alkali metal carbonates, either alone or in admixture with calcite, alkali metal citrates, alkali metal nitrilotriacetates, carboxymethyloxysuccinates, zeolites, polyacetalcarboxylates and so on.

Furthermore, the detergent compositions may contain from 1–35% of a bleaching agent or a bleach precursor or a system comprising bleaching agent and/or precursor with activator therefor. Further optional ingredients are lather boosters, foam depressors, anti-corrosion agents, soil-suspending agents, sequestering agents, anti-soil redeposition agents, perfumes, dyes, stabilising agents for the enzymes and so on.

The compositions can be used for the washing of textile materials, especially but without limitation cotton and polyester-based textiles and mixtures thereof. Especially suitable are for example washing processes carried out at temperatures of about 60–65 deg C. or lower, e.g. about 30 deg C.-35 deg C. or lower. It can be very suitable to use the compositions at a rate sufficient to provide about e.g. 0.4–0.8 g/l surfactant in the wash liquor, although it is of course possible to use lesser or greater concentrations if desired. Without limitation it can for example be stated that a use-rate from about 1 to 10 g/l, e.g. from about 3–6 g/l, of the detergent formulation is suitable for use in the case when the formulations are substantially as in the Examples.

Particular forms of detergent composition within the scope of the invention include:

a) A detergent composition formulated as a detergent powder containing phosphate builder, anionic surfactant, nonionic surfactant, acrylic or equivalent polymer, perborate bleach precursor, amino-containing bleach activator, silicate or other structurant, alkali to adjust to desired pH in use, and neutral inorganic salt.

b) A detergent composition formulated as a detergent powder containing zeolite builder, anionic surfactant, nonionic surfactant, acrylic or equivalent polymer, perborate bleach precursor, amino-containing bleach activator, silicate or other structurant, alkali to adjust to desired pH in use, and neutral inorganic salt.

c) A detergent composition formulated as an aqueous detergent liquid comprising anionic surfactant, nonionic surfactant, humectant, organic acid, caustic alkali, with a pH adjusted to a value between 9 and 10.

d) A detergent composition formulated as a nonaqueous detergent liquid comprising a liquid nonionic surfactant consisting essentially of linear alkoxylated primary alcohol, triacetin, sodium triphosphate, caustic alkali, perborate monohydrate bleach precursor, and tertiary amine bleach activator, with a pH adjusted to a value between about 9 and 10.

e) A detergent composition formulated as a detergent powder in the form of a granulate having a bulk density of at least 600 g/l, containing anionic surfactant and a mixture of nonionic surfactants with respective alkoxylation degrees about 7 and about 3, low or substantially zero neutral inorganic salt, phosphate builder, perborate bleach precursor, tertiary amine bleach activator, sodium silicate, and minors and moisture.

f) A detergent composition formulated as a detergent powder in the form of a granulate having a bulk density of at least 600 g/l, containing anionic surfactant and a mixture of nonionic surfactants with respective alkoxylation degrees about 7 and about 3, low or substantially zero neutral inorganic salt, zeolite builder, perborate bleach precursor, tertiary amine bleach activator, sodium silicate, and minors and moisture.

g) A detergent composition formulated as a detergent powder containing anionic surfactant, nonionic surfactant, acrylic polymer, fatty acid soap, sodium carbonate, sodium sulphate, clay particles, perborate bleach precursor, tertiary amine bleach activator, sodium silicate, and minors and moisture.

h) A detergent composition formulated as a detergent (soap) bar containing soap based on pan-saponified mixture of tallow and coconut oil, neutralised with orthophosphoric acid, mixed with protease, also mixed with sodium formate, borax, propylene glycol and sodium sulphate, and then plodded on a soap production line.

j) An enzymatic detergent composition formulated to give a wash liquor pH of 9 or less when used at a rate corresponding to 0.4–0.8 g/l surfactant.

k) An enzymatic detergent composition formulated to give a wash liquor pH of 8.5 or more when used at a rate corresponding to 0.4–0.8 g/l surfactant.

l) An enzymatic detergent composition formulated to give a wash liquor ionic strength of 0.03 or less, e.g. 0.02 or less, when used at a rate corresponding to 0.4–0.8 g/l surfactant.

m) An enzymatic detergent composition formulated to give a wash liquor ionic strength of 0.01 or more, e.g. 0.02 or more, when used at a rate corresponding to 0.4–0.8 g/l surfactant.

The invention is further illustrated by the following Examples.

EXAMPLES

Example A relates to construction of certain variant proteases within the scope of the present invention, by appropriate rDNA techniques, and to mutated genes, vectors and mutant and transformed microorganisms useful in the production of the proteases.

Example B describes detergent formulations involving the proteases of Example A and gives performance test results therefor.

Examples D1–D14 describe further detergent formulations into which the proteases of the invention can suitably be incorporated.

Example A

I

Many methods for introducing mutations into genes are well known in the art. After a brief discussion of cloning subtilisin genes, methods for generating mutations in both random sites, and specific sites, within the subtilisin gene will be discussed.

The gene encoding subtilisin may be cloned from any Gram-positive bacteria or fungus by various methods, well known in the art. First a genomic, and/or cDNA library of DNA must be constructed using chromosomal DNA or messenger RNA from the organism that produces the subtilisin to be studied. Then, if the amino acid sequence of the subtilisin is known, homologous, labelled oligonucleotide probes may be synthesized and used to identify subtilisin-encoding clones from a genomic library of bacterial DNA, or from a fungal cDNA library. Alternatively, a labelled oligonucleotide probe containing sequences homologous to subtilisin from another strain of bacteria or fungus could be used as a probe to identify subtilisin-encoding clones, using hybridization and washing conditions of lower stringency.

Yet another method for identifying subtilisin-producing clones involves inserting fragments of genomic DNA into an expression vector, such as a plasmid, transforming protease-negative bacteria with the resulting genomic DNA library, and then plating the transformed bacteria onto agar containing a substrate for subtilisin, such as skim milk. Those bacteria containing subtilisin-bearing plasmid will produce colonies surrounded by a halo of clear agar, due to digestion of the skim milk by excreted subtilisin.

Once the subtilisin gene has been cloned into a suitable vector, such as a plasmid, several methods can be used to introduce random mutations into the gene. One method is to incorporate the cloned subtilisin gene as part of a retrievable vector, into a mutator strain of Eschericia coli.

Another method involves generating a single stranded form of the subtilisin gene, and then annealing the fragment of DNA containing the subtilisin gene with another DNA fragment such that a portion of the subtilisin gene remains single stranded. This discrete, single stranded region is then exposed to any of a number of mutagenic agents, including, but not limited to, sodium bisulfite, hydroxylamine, nitrous acid, formic acid, or hydralazine. A specific example of this method for generating random mutations is described by Shortle and Nathans (1978, Proc. Natl. Acad. Sci. U.S.A., 75: 2170–2174). According to the method of Shortle and Nathans, the plasmid bearing the subtilisin gene is nicked by a restriction enzyme that cleaves within the gene. This nick is widened into a gap using the exonuclease action of DNA polymerase I. The resulting single stranded gap is then mutated using any one of the above mentioned mutagenic agents.

Alternatively, the subtilisin gene from a Bacillus species including the natural promoter and other control sequences is cloned into a plasmid vector containing replicons for both E. coli and B. subtilis, a selectable phenotypic marker and the M13 origin of replication for production of single-stranded plasmid DNA upon superinfection with helper phage IR1. Single-stranded plasmid DNA containing the cloned subtilisin gene is isolated and annealed with a DNA fragment containing vector sequences but not the coding region of subtilisin, resulting in a gapped duplex molecule. Mutations are introduced into the subtilisin gene either with sodium bisulfite, nitrous acid or formic acid or by replication in a mutator strain of E. coli as described above. Since sodium bisulfite reacts exclusively with cytosine in a single-stranded DNA, the mutations created with this mutagen are restricted only to the coding regions. Reaction time and bisulfite concentration are varied in different experiments such that from one to five mutations are created per subtilisin gene on average. Incubation of 10 micro-g of gapped duplex DNA in 4M Na-bisulfite, pH. 6.0, for 9 minutes at 37 deg C. in a reaction volume of 400 micro-l deaminates about 1% of cytosines in the single-stranded region. The coding region of mature subtilisin contains about 200 cytosines, depending on the DNA strand. Advantageously, the reaction time is varied from about 4 minutes (to produce a mutation frequency of about one in 200) to about 20 minutes (about 5 in 200).

After mutagenesis the gapped molecules are treated in vitro with DNA polymerase I (Klenow fragment) to make fully double-stranded molecules and fix the mutations. Competent *E. coli* are then transformed with the mutagen-treated DNA to produce an amplified library of mutant subtilisins. Amplified mutant libraries can also be made by growing the plasmid DNA in a Mut D strain of *E. coli* which increases the range of mutations due to its error prone DNA polymerase.

The mutagens nitrous acid and formic acid may also be used to produce mutant libraries. Because these chemicals are not as specific for single-stranded DNA as sodium bisulfite, the mutagenesis reactions are performed according to the following procedure. The coding portion of the subtilisin gene is cloned in M13 phage by standard methods and single stranded phage DNA prepared. The single-stranded DNA is then reacted with 1M nitrous acid pH. 4.3 for 15–60 minutes at 23 deg C. or 2.4M formic acid for 1–5 minutes at 23 deg C. These ranges of reaction times produce a mutation frequency of from 1 in 1000 to 5 in 1000. After mutagenesis, a universal primer is annealed to the M13 DNA and duplex DNA is synthesized using the mutagenized single-stranded DNA as a template so that the coding portion of the subtilisin gene becomes fully double stranded. At this point the coding region can be cut out of the M13 vector with restriction enzymes and ligated into an unmutagenized expression vector so that mutations occur only in the restriction fragment. (Myers et al, Science 229 (1985) 242–257).

Once the subtilisin gene has been cloned, and desirable sites for mutation identified, these mutations can be introduced using synthetic oligonucleotides. These oligonucleotides contain nucleotide sequences flanking the desired mutation sites; mutant nucleotides are inserted during oligonucleotide synthesis.

In a preferred method, a single stranded gap of DNA, bridging the subtilisin gene, is created in a vector bearing the subtilisin gene. Then the synthetic nucleotide, bearing the desired mutation, is annealed to a homologous portion of the single-stranded DNA. The remaining gap is then filled in by DNA polymerase I (Klenow fragment) and the construct is ligated using T4 ligase. A specific example of this method is described in Morinaga et al, (Biotechnology 2 (1984) 646–639). According to Morinaga et al, a fragment within the gene is removed using restriction endonuclease. The vector/gene, now containing a gap, is then denatured and hybridized to a vector/gene which, instead of containing a gap, has been cleaved with another restriction endonuclease at a site outside the area involved in the gap. A single-stranded region of the gene is then available for hybridization with mutated oligonucleotides, the remaining gap is filled in by the Klenow fragment of DNA polymerase I, the insertions are ligated with T4 DNA ligase, and, after one cycle of replication, a double-stranded plasmid bearing the desired mutation is produced. The Morinaga method obviates the additional manipulation of constructing new restriction sites, and therefore facilitates the generation of mutations at multiple sites.

U.S. Pat. No. 4,760,025, (Estell et al, Jul. 26, 1988) shows how to introduce oligonucleotides bearing multiple mutations by performing minor alterations of the cassette, however, an even greater variety of mutations can be introduced at any one time by the Morinaga method, because a multitude of oligonucleotides, of various lengths, can be introduced.

In carrying out the present invention, a mutated subtilisin gene as defined above can be produced by analogues of methods described above, or any alternative methods known in the art, and can be expressed, in enzyme form, using an expression vector. An expression vector generally falls under the definition of a cloning vector, since an expression vector usually includes the components of a typical cloning vector, namely, an element that permits autonomous replication of the vector in a microorganism independent of the genome of the microorganism, and one or more phenotypic markers for selection purposes. An expression vector includes control sequences encoding a pronoter, operator, ribosome binding site, translation initiation signal, and, optionally, a repressor gene or various activator genes.

To permit the secretion of the expressed protein, nucleotides encoding a "signal sequence" may be inserted prior to the coding sequence of the gene. For expression under the direction of control sequences, a target gene to be treated according to the invention is operably linked to the control sequences in the proper reading frame. Promoter sequences that can be incorporated into plasmid vectors, and which can support the transcription of the mutant subtilisin gene, include but are not limited to the prokaryotic beta-lactamase promoter (Villa-Kamaroff et al, Proc. Nat. Acad. Sci. U.S.A. 75 (1978) 3727–3731) and the tac promoter (DeBoer et al, Proc. Natl. Acad. Sci. USA. 80 (1983) 21–25). Further references can also be found in "Useful proteins from recombinant bacteria", in Scientific American, 242 (1980) 74–94.

According to one embodiment *B. subtilis* is transformed by an expression vector carrying the mutated DNA. If expression is to take place in a secreting microorganism such as *B. subtilis* a signal sequence may follow the translation initiation signal and precede the DNA sequence of interest. The signal sequence acts to transport the expression product to the cell wall where it is cleaved from the product upon secretion. The term "control sequences" as defined above is intended to include a signal sequence, when it is present.

II

In the following example showing a presently preferred method for constructing and expressing genes to code for wild-type and variant protease enzymes in accordance with embodiments of the present invention, the following materials are referred to:

*B. subtilis* 309 and 147 are variants of *Bacillus lentus*, deposited with the NCIB and accorded the accession numbers NCIB 10147 and NCIB 10309, and described in U.S. Pat. No. 3,723,250 incorporated by reference herein.

*E. coli* MC 1000 (M. J. Casadaban and S. N. Cohen, J. Mol Biol. 138 (1980) 179–207), was made r-m+ by conventional methods and is also described in U.S. patent application Ser. No. 039,298.

A vector suited to a synthetic gene coding for subtilisin 309 and its mutants was constructed. It is essentially a pUC19 plasmid (see C. Yanish-Perron and J. Messing, Gene 33 (1985) 103–119), in which the multiple cloning site has been replaced by a linker containing the restriction sites used to separate the five sub-fragments constituting the gene. The new linker was inserted into Eco RI-Hin dIII cut pUC19 thereby destroying these sites.
(RI) KpnI PstI EcoRI Hind3 ClaI SphI Bam (H3)
AATTGGTACCCTGCAGGAATTCAAGCT-
 TATCGATGGCATGCGGATCC
CCATGGGACGTCCTTAAGTTCGAATAGC-
 TACCGTACGCCTAGGTCGA A synthetic gene coding for the mature part of subtilisin 309' was constructed as shown by the following drawings. The gene was synthesized from fragments. Each subfragments was made from 6 to 12 oligonucleotides. The oligonucleotides were synthesised on an automatic DNA synthesiser using phosphoramidite chemistry on a controlled glass support (see S. L. Beaucage and M. H. Carruthers, Tetrahedron Letters 22 (1981) 1859–1869). Duplexes were formed from corresponding pairs of oligonucleotides by heating for 5 min at 90 deg C. followed by cooling to room temperature over a period of 75 min. The duplexes were mixed and treated with T4 DNA ligase.

The five subfragments were isolated on a 2% agarose gel and inserted into pSX191. The sequence was verified by dideoxynucleotide sequencing. Fragments A–E were isolated and ligated together with KpnI-BamHI cut pXS191. The ligation mixtures were used to transform competent *E. coli* MC1000 r-,m+ selecting for ampicillin resistance. The 850 bp KpnI-BamHI fragment that constitutes the part of the subtilisin 309 gene coding for the mature part of the enzyme was then used to replace the wild type gene on pSX212 giving rise to pSX222, which was then transformed into competent *B. subtilis* SHa273. After fermentation of the transformed strain and purification of the enzyme it was shown that the product was indistinguishable from the wild type product.

Protease variants derived from the synthetic gene are made by using oligonucleotides with altered sequence at the place(s) where mutation is wanted (e.g. with sequences as given below) and mixing them with the rest of the oligonucleotides appropriate to the synthetic gene. Assembly of the variant gene is carried out with the variant materials in a manner otherwise analogous to that described above. Further information on synthetic genes generally is available in Agarval et al, Nature 227 (1970) 27–34.

A KpnI site was introduced into the beginning of the subtilisin 309 synthetic gene encoding the mature part of the enzyme. The method used is called oligonucleotide directed double-strand break repair mutagenesis and is described by Wlodek Mandecki in Proc. Nat. Acad. Sci. USA. 83 (1986) 7177–7181. pSX172 is opened with NcoI at the beginning of the mature part of the subtilisin 309 gene and the KpnI site is introduced right in front of NcoI by changing two bases without changing the amino acid sequence. pSX172 is described in European patent Application EP 0 405 901. The KpnI site so created is inserted into pSX120 on a 400-bp PvuI-NheI fragment, giving rise to pSX212. pSX120 is also described in European Patent Application EP 0 405 901.

The synthetic gene is inserted between KpnI and BamHI on pSX212, giving rise to pSX222.

The resulting product is mixed with a suitable oligonucleotide heated to 100 deg C., cooled to 0 deg C., and transformed into *E. coli*. After retransformation, the recombinants can be screened by colony hybridisation using the suitable oligonucleotide 32-P-labelled form.

Examples of mutations and corresponding oligonucleotides are as follows: A2-02/A3-01: K27R; B1-02: E54D; B4-03: Y91F, K94R; D1-01/D2-02: Y167E, Y171V; D3-04: Y192E; D4-01/D5-01: Y209F, Y214T; E2-01: K235R, K237R; E3-01: K251E; E4-02: Y263F. Such oligonucleotides appropriate to the introduction of mutations as described herein can have sequences for example as follows:

K27R (overlap between A2 and A3)
```
                5'-GTAAGAGTTGCTGTCCTCGATACAGGGATA-3'
                    | | | | * |
3'-TTGGCACCTAACTGTCCAAGACCACATTCT-5'
```

E54D (fragment B1)
```
5'-AGCTTTGTACCAGGGGATCCGTCGACTCAAGATGGG-3'
   | | | | | | | | | | | | | | * | | | | | | | | | | | | | | | | | | |
      5'-AACATGGTCCCCTAGGCAGCTGAGTTCTACCCTTACCC-5'
```

Y91F, K94R (fragment B4)
```
5'-GTAGCGCCGAGCGCTGAGCTATTCGCTGTTAGAGTC-3'
   | | | | | | | | | | | | | | | | * | | | | | | | | * | | | |
     3'-GGCTCGCGACTCGATAAGCGACAATCTCAGGATCCCCGC-5'
```

Y167E, Y171V (fragments D1 and D2)
```
5'-AATTCAGGTGCAGGCTCAATCAGCGAACCGGCG-3'                continues
   | | | | | | | | | | | | | | | | | | | | | | | | |*** | | | | | |   | |**|
       3'-GTCCACGTCCGAGTTAGTCGCTTGGCCGCGCGCAA-5'
5'-CGCGTYGCGAACGCAATGGCAGTCGGAGCTACTGATCAAAAC-3'
   | | |**|
```

Y167F, Y171V (fragments D1 and D2)
```
5'-AATTCAGGTGCAGGCTCAATCAGCTTTCCGGCT-3'      continues
   | | | | | | | | | | | | | | | | | | | | | |*| | | | | | | | | |** |
       3'-GTCCACGTCCGAGTTAGTCAAAGGCCGAGCGCAA
5'-CGCGTTGCGAACGCAATGGCAGTCGGAGCTACTGATCAAAAC-3'
   | | |**|
```

Y192E (fragment D3)
```
5'-AACAACCGCGCTAGCTTTTCACAGGAAGGCGCAGGC-3'
   | | | | | | | | | | | | | | | | | | | | | |*|*| | | | | | | | |
       GCGCGATCGAAAAGTGTCCTTCCGCGTCCGGAACTG-5'
```

Y192F (fragment D3)

-continued
```
5'-AACAACCGCGCTAGCTTTTCACAGTTGGAGCAGGC-3'
   ||||||||||||||||||*|||*|||||||
              3'-GCGCGATCGAAAAGTGTAAACCTCGTCCGAATCG-5'
```

Y209F, Y214T (fragments D4 and D5)
```
                                                   |*||||
3'-TAACAGCGTGGGCCCCATTTGCACGTCTCGTGTAAGGGT-5' continues
5'-TTCCCAGGTTCAACAACTGCCAGCTTAAACGGTACAT-3'
   |*|||||||||||||**|||||||||||||||||||
       CCAAGTTGTTGACGGTCGAATTTGCCATGTAGC-5'
```

K235R, K237R (fragment E2)
```
5'-CTTGTTAGACAAAGGAACCCATCTTGGTCTAATGTACAA-3'
   |*|||||*|||||||||||||||||||||||||||
     TCTGTTTCCTTGGGTAGAACCAGATTACATGTTTAAGCT-5'
```

K251E (fragment E3)
```
5'-ATTCGAAATCATCTAGAGAATACGGCAACTCGTTTA-3'
   |||||||||*|||||||||||||||||||||||
       3'-TTAGTAGATCTCTTATGCCGTTGATCAAATCCTTCGTGC-5'
```

Y263F (fragment E4)
```
5'-GGAAGCACGAACTTGTTTGGAAGCGGACTTGTTAACGCA-3'
   |||||||*|||||||||||||||||||||||||
       3'-TTGAACAAACCTTCGCCTGAACAATTGCGTCTTCGC-5'
```

These oligonucleotides were combined with the rest of the oligonucleotides from the synthetic gene that were not changed. The mutated fragments A, B, D, and E were ligated together with fragment C where there were no changes needed for the variants under construction.

III

Corresponding variants based on subtilisin 147 can be made in analogous manner, and the transformed *B. subtilis* subjected to fermentation and post-processing to purify the wanted enzyme.

IV

The following applicable purification procedure relates to a typical purification of a 10 liter scale fermentation of the Subtilisin 147 enzyme, the Subtilisin 309 enzyme or mutants thereof.

Approximately 8 liters of fermentation broth are centrifuged at 5000 rpm for 35 minutes in 1 liter beakers. The supernatants are adjusted to pH 6.5 using 10% acetic acid and filtered on Seitz Supra S100 filter plates.

The filtrates are concentrated to approximately 400 ml using an Amicon CH2A UF unit equipped with an Amicon SLY10 UF cartridge. The UF concentrate is centrifuged and filtered prior to absorption at room temperature on a Bacitracin affinity column at pH 7. The protease is eluted from the Bacitracin column at room temperature using 25% 2-propanol and 1M sodium chloride in a buffer solution with 0.01 dimethylglutaric acid, 0.1M boric acid and 0.002M calcium chloride adjusted to pH 7.

The fractions with protease activity from the Bacitracin purification step are combined and applied to a 750 ml Sephadex G25 column (5 cm dia.) equilibrated with a buffer containing 0.01 dimethylglutaric acid, 0.2M boric acid and 0.002 m calcium chloride adjusted to pH 6.5.

Fractions with proteolytic activity from the Sephadex G25 column are combined and applied to a 150 ml CM Sepharose CL 6B cation exchange column (5 cm dia.) equilibrated with a buffer containing 0.01M dimethylglutaric acid, 0.2M boric acid, and 0.002M calcium chloride adjusted to pH 6.5.

The protease is eluted using a linear gradient of 0-0.1M sodium chloride in 2 liters of the same buffer (0-0.2M sodium chloride in case of sub 147).

In a final purification step protease containing fractions from the CM Sepharose column are combined and concentrated in an Amicon ultrafiltration cell equipped with a GR81PP membrane (from the Danish Sugar Factories Inc.).

Example B

Titration curves and wash performance of some representative examples of the proteases and detergent compositions according to the present invention are as follows:

Mutant protease enzymes A, B and C, formed by the methods described in Example A, have been tested. Their amino acid sequence corresponds to that of subtilisin 309, with the following mutations:

Protease

A: K27R
B: K235R+K237R+K251E+Y263F
C: E54D+Y91F+K94R

Further mutants include:

D: K27R+E54D+Y91F+K94R+Y209F+Y214T+K235R+ K237R+K251E+Y263F
E: K27R+E54D+Y91F+K94R+Y167F+Y171V+Y192F+ Y209F+Y214T+K235R+K237R+K251E+Y263F
F: as mutant E with two further mutations adding the charge of a D residue and one adding the charge of an E residue
G: as mutant F with further mutation of histidines at positions 17,39,120,226 to neutral residues
H: as mutant G with the N-terminal chemically modified (blocked) to give a neutral group.

The proteolytic activity of the mutant enzymes can be assayed by the dimethyl casein (DMC) method described in NOVO Publication AF 220-gb (or later editions), available from NovoNordisk A/S, Bagsvaerd, Denmark, which publication is hereby included by reference.

Wash tests have been carried out in the following detergent system: The wash liquor was a 0.83 g/l solution at 20 deg C. derived from the following detergent formulation (% by wt):

| | |
|---|---|
| Sodium linear alkylbenzene sulphonate | 25 |
| AS | 7 |
| AES | 2 |
| AOS | 2 |
| Soap | 3 |
| AE | 2 |
| Zeolite A | 22 |
| Sodium silicate | 5 |
| Sodium sulphate | 4 |
| Polyethyleneglycol | 2 |
| Sodium carbonate | 17 |

Test cloths (2.2cm×2.2cm), approximately 0.1 g) are produced by passing desized cotton (100% cotton, DS 71) cloth through the vessel in a Mathis Washing and Drying Unit type TH (Werner Mathis AG, Zurich, Switzerland) containing grass juice. Finally the cloth is dried in a strong air stream at room temperature, stored at room temperature for 3 weeks, and subsequently kept at −18 deg C. prior to use.

All tests are performed in a model miniwash system. In this system 6 test cloths are washed in a 150 ml beaker containing 60 ml of detergent solution. The beakers are kept in a thermostat water bath at 20 deg C with magnetic stirring.

The washings are performed for 10 minutes, and subsequent to the washing the cloths are rinsed in running tap-water for 25 minutes in a bucket.

The cloths are then air-dried overnight (protected against daylight) and the reflectance, R, determined on an ELREPHO 2000 photometer from Datacolor S. A., Dietkikon, Switzerland at 460 nm.

As a measure of the wash performance differential reflectance, delta R, is used, being equal to the reflectance after wash with enzyme added minus the reflectance after wash with no enzyme added.

The improvement factor is calculated from a dose-response curve, and relates to the amount of enzyme needed for obtaining a given delta R value in comparison to the wild type enzyme in question. Here, the performance of the enzymes was compared with that of 'wild type' subtilisin 309 ('wt'). For example, an improvement factor of 2 indicates that only half the amount of enzyme is needed to obtain the same delta R value.

Results were as follows:

| | | Improvement factors at indicated pH: | | | |
|---|---|---|---|---|---|
| Protease: | pI(calc) | pH: 8 | 9 | 10 | 11 |
| wt | 10.1 | | | | |
| A | 10.2 | <1 | <1 | 2.3 | 1.3 |
| B | 9.6 | 1.4 | 1.3 | 3.6 | 1.9 |
| C | 10.4 | <1 | <1 | 1.8 | 2.2 |
| a + g' | 10.1 | 1.2 | 1.4 | 1.4 | 1.0 |

The preferred example of these mutant proteases is protease B, showing the least steep titration curve and the largest improvement factor with respect to the wild type enzyme.

The following further non-limitative examples show detergent formulations in accordance with the invention:

Detergent D1

A detergent powder according to an embodiment of the invention containing phosphate builder is formulated to contain: total active detergent about 16%, anionic detergent about 9%, nonionic detergent about 6%, phosphate-containing builder about 20%, acrylic or equivalent polymer about 3.5% (alternatively down to about 2%), perborate bleach precursor about 6–18%, alternatively about 15–20%, amino-containing bleach activator about 2%, silicate or other structurant about 3.5%, alternatively up to about 8%, enzyme of about 8 glycine units/mg activity, with alkali to adjust to desired pH in use, and neutral inorganic salt, and enzymes (about 0.5% each enzyme).

The anionic detergent is a mixture of sodium dodecylbenzene sulphonate, alternatively sodium linear alkyl-benzene-sulphonate, 6%, and primary alkyl sulphate 3%. The nonionic detergent is an ethoxylate of an approx. C13–C15 primary alcohol with 7 ethoxylate residues per mole. The phosphate builder is sodium tripolyphosphate. The polymer is polyacrylic acid, alternatively acrylic/maleic copolymer. The perborate bleach precursor is sodium tetraborate tetrahydrate or monohydrate. The activator is tetra-acetyl-ethylene-diamine. The structurant is sodium silicate. The neutral inorganic salt is sodium sulphate. The enzymes comprise protease B described above.

Detergent D1a

A detergent powder according to an embodiment of the invention containing phosphate builder is formulated to contain: total active detergent about 15%, anionic detergent about 7%, nonionic detergent about 6%, phosphate-containing builder about 25%, acrylic or equivalent polymer about 0.5%, perborate bleach precursor about 10%, amino-containing bleach activator about 2%, silicate or other structurant about 6%, protease enzyme of about 8 glycine units/mg grade, with alkali to adjust to desired pH in use, and neutral inorganic salt, and enzymes (about 0.5% each enzyme).

The anionic detergent is sodium linear alkyl-benzene-sulphonate. The nonionic detergent is an ethoxylate of an approx. C13–C15 primary alcohol with 7 ethoxylate residues per mole or a mixture of this with the corresponding alcohol ethoxylated to the extent of 3 residues per mole. The phosphate builder is sodium tripolyphosphate. The perborate or peracid bleach precursor is sodium tetraborate tetrahydrate. The activator is tetra-acetyl-ethylene-diamine. The structurant is sodium silicate. The neutral inorganic salt is sodium sulphate. The enzymes comprise protease B described above.

Detergent D2

A detergent powder according to an embodiment of the invention containing zeolite builder is formulated to contain: total active detergent about 16%, anionic detergent about 9%, nonionic detergent about 6%, zeolite-containing builder about 20%, acrylic or equivalent polymer about 3.5%, perborate bleach precursor about 6–18% amino-containing bleach activator about 2%, silicate or other structurant about 3.5%, alternatively down to about 2.5%, enzyme of about 8 (alternatively about 15) glycine units/mg grade, with alkali to adjust to desired pH in use, and neutral inorganic salt, and enzymes (about 0.5% each enzyme).

The anionic detergent is a mixture of sodium dodecylbenzene sulphonate, alternatively sodium linear alkyl-benzene-sulphonate, 6% and primary alkyl sulphate 3%. The nonionic detergent is an ethoxylate of an approx. C13–C15 primary alcohol with 7 ethoxylate residues per mole. The zeolite builder is type A zeolite. The polymer is polyacrylic acid. The perborate bleach precursor is sodium tetraborate tetrahydrate or monohydrate. The activator is tetraacetyl-ethylenediamine. The structurant is sodium silicate. The neutral inorganic salt is sodium sulphate. The enzymes comprise protease B described above.

Detergent D2a

A detergent powder according to an embodiment of the invention containing zeolite builder is formulated to contain: total active detergent about 14%, anionic detergent about 7%, nonionic detergent about 7%, zeolite-containing builder about 25%, acrylic or equivalent polymer about 3%, perborate or peracid bleach precursor about 10%, amino-containing bleach activator about 2%, silicate or other structurant about 0 5%, enzyme of about 6 glycline units/mg grade, with alkali to adjust to desired pH in use, and neutral inorganic salt, and enzymes (about 0.5% each enzyme).

The anionic detergent is sodium linear alkyl-benzenesulphonate, the nonionic detergent is a mixture of ethoxylates of an approx. C13–C15 primary alcohol with 7 and 3 ethoxylate residues respectively per mole. The zeolite builder is type A zeolite. The polymer is an acrylic/maleic copolymer. The perborate bleach precursor is sodium tetraborate monohydrate. The activator is tetra-acetyl-ethylene-diamine. The structurant is sodium silicate. The neutral inorganic salt is sodium sulphate. The enzymes comprise protease B described above.

Detergent D3

An aqueous detergent liquid according to an embodiment of the invention is formulated to contain: Dodecylbenzenesulphonic acid 16%, C12–C15 linear alcohol condensed with 7 mol/mol ethylene oxide 7%, monoethanolamine 2%, citric acid 6 5%, sodium xylenesulphonate 6%, sodium hydroxide about 4.1%, protease 0.5%, minors and water to 100%. The pH is adjusted to a value between 9 and 10. The enzyme comprises protease B and/or C described above.

Detergent D4

A nonaqueous detergent liquid according to an embodiment of the invention is formulated using 38.5% C13–C15 linear primary alcohol alkoxylated with 4.9 mol/mol ethylene oxide and 2.7 mol/mol propylene oxide, 5% triacetin, 30% sodium triphosphate, 4% soda ash, 15.5% sodium perborate monohydrate containing a minor proportion of oxoborate, 4% TAED, 0.25% EDTA of which 0.1% as phosphonic acid, Aerosil 0.6%, SCMC 1%, and 0.6% protease. The pH is adjusted to a value between 9 and 10, e.g. about 9.8. The enzyme comprises protease B and/or C described above.

Detergent D5

A detergent powder according to an embodiment of the invention is formulated in the form of a granulate having a bulk density of at least 600 g/l, containing about 20% by weight surfactant of which about 10% is sodium dodecylbenzene sulphonate, and the remainder is a mixture of Synperonic A7 and Synperonic A3 (about 5.5% to 4.5%), and zero neutral inorganic salt (e.g. sodium sulphate), plus phosphate builder about 33%, sodium perborate tetrahydrate about 16%, TAED activator about 4.5%, sodium silicate about 6%, and minors including sodium carbonate about 2%, and moisture content about 10%. Enzymes (about 0.5% each enzyme) are included. The enzyme comprises protease B described above.

Detergent D6

A detergent powder according to an embodiment of the invention is formulated in the form of a granulate having a bulk density of at least 600 g/l, alternatively about 550 g/l, containing about 20%, alternatively about 16%, by weight surfactant of which about 9%, alternatively about 7%, is sodium dodecylbenzene sulphonate, alternatively sodium linear alkyl benzene sulphonate, and the remainder is a mixture of Synperonic A7 and Synperonic A3 (or similar ethoxylates) (respectively about 5% & 6%, alternatively about 4% and 7%), and zero neutral inorganic salt (e.g. sodium sulphate), plus zeolite builder about 30%, alternatively about 25%, sodium perborate tetrahydrate, alternatively monohydrate, about 14% or 15%, TAED activator about 3.6%, and minors including sodium carbonate about 9%, or up to 15%, Dequest 2047 about 0 7% and moisture content about 10%. Enzymes (about 0.5% each enzyme, or about 0.2% lipase and about 0.7% protease) are included. The enzyme comprises protease B described above.

Detergent D6a

A detergent powder according to an embodiment of the invention is formulated in the form of a granulate having a bulk density of at least 600 g/l, containing about 15% by weight surfactant of which about 7% is sodium linear alkyl benzene sulphonate, 2% primary alcohol sulphate and the remainder Synperonic A7 or similar ethoxylate, and zero neutral inorganic salt (e.g. sodium sulphate), plus zeolite builder about 22%, sodium perborate tetrahydrate about 15%, TAED activator about 7° and minors including sodium carbonate about 15%, Dequest 2047 about 0.7%, and moisture content about 10%. Enzymes (about 1.2%) include protease B described above.

Detergent D7

A detergent powder according to an embodiment of the invention is formulated to contain: Dodecylbenzenesulphonic acid 6%, C12–C15 linear alcohol condensed with 7 mol/mol ethylene oxide 5%, fatty acid soap 3%, Sokolan CP5 polymer 3%, zeolite A 22%, sodium carbonate 10%, sodium sulphate 17%, clay particles 8%, sodium perborate tetrahydrate 13%, tetraacetyl-ethylenediamine 2%, protease 0.5%, minors and water to 100%. The pH is adjusted to a value between 9 and 10. The protease enzyme comprises protease B described above.

Detergent D8

A detergent (soap) bar according to an embodiment of the invention is formulated as follows: soap based on pansaponified 82% tallow, 18% coconut oil, neutralised with 0.15% orthophosphoric acid, mixed with protease (about 8 GU/mg of the bar composition) and mixed with sodium formate 2%, borax 2%, propylene glycol 2% and sodium sulphate 1%, is then plodded on a soap production line. The protease enzyme comprises protease B and/or C as described above.

Detergent D9

Structured liquid detergents can for example contain, in addition to a protease as described herein, 2–15% nonionic surfactant, 5–40% total surfactant, comprising nonionic and optionally anionic surfactant, 5–35% phosphate-containing or non-phosphatecontaining builder, 0.2–0.8% polymeric thickener, e.g. crosslinked acrylic polymer with m.w. over 106, at least 10% sodium silicate, e.g. as neutral waterglass, alkali (e.g. potassium containing alkali) to adjust to desired pH, preferably in the range 9–10 or upwards, e.g. above pH 11, with a ratio sodium cation: silicate anion (as free silica) (by weight) less than 0.7:1, and viscosity of 0.3–30 Pas (at 20 deg C. and 20 s-1).

Suitable examples contain about 5% nonionic surfactant C13–15 alcohol alkoxylated with about 5 EO groups per mole and with about 2.7 PO groups per mole, 15–23% neutral water-glass with 3.5 weight ratio between silica and sodium oxide, 13–19% KOH, 8–23% STPP, 0–11% sodium carbonate, 0.5% carbopol 941.

Protease may be incorporated at for example 0.5% of protease B described above.

Detergent D10

A structured, viscous, aqueous liquid detergent suitable for laundry use is formulated as follows (% by weight):

| | |
|---|---|
| Citric acid | 2.5 |
| Borax (10aq) | 4 |
| NaOH | 2 |
| Glycerol | 5 |
| C14–C15 Linear alkyl-benzene-sulphonate, or C14–15 primary alcohol sulphate | 6.5 |
| Synperonic A3 Nonionic C12–C15 3EO | 1.2 |
| Synperonic A7 Nonionic C12–C15 7EO | 3.6 |
| Zeolite | 20 |
| Protease | 0.5 |
| Amylase (Termamyl 300LDX) | 0.2 |
| minors and water | to 100% |

The pH can be adjusted to a value between 9 and 10. The enzyme is protease B described above.

Detergent D11

An isotropic aqueous liquid detergent suitable for laundry use is formulated as follows (% by weight):

| | |
|---|---|
| Citric acid | 2 |
| Boric acid | 1 |
| NaOH | 3 |
| KOH | 4.5 |
| Glycerol | 10 |
| Ethanol | 6.5 |
| Nonionic surfactant (C12-alcohol 6.5 EO ethoxylate groups/mol) (or sodium primary alcohol sulphate) | 10 |
| Oleic acid | 16 |
| Coconut oil (C12) soap | 11 |
| Protease | 0.5 |
| minors and water | to 100% |

The pH can be adjusted to a value between 9 and 10. The enzyme is protease B and/or C as described above.

Detergent D12

An aqueous liquid detergent composition is formulated to contain:

| | |
|---|---|
| Sodium alkyl-benzene-sulphonate | 14.5 |
| C18 sodium soap | 2 |
| Nonionic detergent (C12–15 6EO) | 9 |
| Fatty acid (oleic acid) | 4.5 |
| sodium alkenyl succinate | 11 |
| propanediol | 1.5 |
| ethanol | 3.6 |
| sodium citrate | 3.2 |
| Complexing agent e.g. Dequest 2060 | 0.7 |
| Protease | 0.5 |
| Amylase | 0.1 |
| Sodium chloride | 0.5 |
| minors and water | to 100% |

The pH can be adjusted to a value between 9 and 10. The enzyme is protease B and/or C as described above.

Detergent D13

An aqueous liquid detergent composition is formulated to contain:

| | |
|---|---|
| sodium alkyl-benzene-sulphonate | 8 |
| nonionic detergent 6.5EO | 10 |
| Oleic diethylamide | 10 |
| Fatty acid (C12/C18 75:25) | 18 |
| sodium citrate | 1 |
| triethanolamine | 5 |
| propanol | 7 |
| ethanol | 5 |
| Dequest 2060 | 0.5 |
| Protease | 0.5 |
| Amylase | 0.1 |
| minors and water | to 100% |

The pH can be adjusted to a value between 9 and 10. The enzyme is protease B and/or C as described above.

Detergent D14

A non-aqueous liquid detergent composition is formulated to contain (% by weight):

| | |
|---|---|
| Liquid nonionic detergent (C10-12, 6.2EO) | 41% |
| triacetin | 5 |
| linear alkylbenzenesulphonic acid | 6 |
| magnesium oxide stabiliser | 1 |
| Sodium carbonate builder/base | 18 |
| Calcium carbonate builder | 8 |
| bleach activator TAED | 3.5 |
| bleach precursor perborate monohydrate | 10.5 |
| partly-hydrophobic silica | 2 |
| protease | 0.4 |
| lipase (Lipolase) | 3 |
| minors or additional liquid nonionic surfactant (no water) | to 100% |

In formulating this composition, the liquid nonionic surfactant and triacetin are added first, followed by the magnesium oxide, then the other ingredients except enzyme. The mixture is milled in a colloid mill and cooled, and finally the enzyme(s) and any other heat-sensitive minors are added.

The enzyme is protease B described above.

Also usable are any one of the detergent formulations described and exemplified in EP 0 342 177 in conjunction with for example protease B described above.

Although the present invention has been discussed and exemplified in connection with various specific embodiments thereof this is not to be construed as a limitation to the applicability and scope of the disclosure, which extends to all combinations and subcombinations of features mentioned and described in the foregoing as well as in the attached claims.

We claim:

1. A modified subtilisin comprising a mutation in an amino acid sequence of a subtilisin at a position numbered according to the amino acid sequence of the mature subtilisin BPN', wherein the mutation is selected from the group consisting of:
   (a) a histidine at position 17 substituted by a glutamine,
   (b) a histidine at position 39 substituted by a serine,
   (c) a glutamic acid at position 54 substituted with an aspartic add,
   (d) a histidine at position 120 substituted with an asparagine,
   (e) a tyrosine at position 167 substituted with a glutamic acid,
   (f) a tyrosine at position 167 substituted with a phenylalanine,
   (g) a tyrosine at position 171 substituted with a phenylalanine,
   (h) a tyrosine at position 171 substituted with a valine,
   (i) a tyrosine at position 192 substituted with a glutamic acid,
   (j) a tyrosine at position 192 substituted with a phenylalanine,
   (k) a tyrosine at position 209 substituted with a phenylalanine,
   (l) a tyrosine at position 214 substituted with a phenylalanine,
   (m) a histidine at position 226 substituted with a serine, and
   (n) a tyrosine at position 263 substituted with a phenylalanine.

2. The modified subtilisin according to claim 1, wherein the mutation is H17Q.

3. The modified subtilisin according to claim 1, wherein the mutation is H39S.

4. The modified subtilisin according to claim 1, wherein the mutation is E54D.

5. The modified subtilisin according to claim 1, wherein the mutation is H120N.

6. The modified subtilisin according to claim 1, wherein the mutation is Y167E.

7. The modified subtilisin according to claim 1, wherein the mutation is Y167F.

8. The modified subtilisin according to claim 1, wherein the mutation is Y171F.

9. The modified subtilisin according to claim 1, wherein the mutation is Y171V.

10. The modified subtilisin according to claim 1, wherein the mutation is Y192E.

11. The modified subtilisin according to claim 1, wherein the mutation is Y192F.

12. The modified subtilisin according to claim 1, wherein the mutation is Y209F.

13. The modified subtilisin according to claim 1, wherein the mutation is Y214F.

14. The modified subtilisin according to claim 1, wherein the mutation is H226S.

15. The modified subtilisin according to claim 1, wherein the mutation is Y263F.

16. The modified subtilisin according to claim 1, further comprising a second mutation in the amino acid sequence of the subtilisin, wherein the second mutation is selected from the group consisting of
   (a) a lysine at position 27 substituted with an arginine,
   (b) a tyrosine at position 91 substituted with a phenylalanine,
   (c) a lysine at position 94 substituted with an arginine,
   (d) a histidine at position 120 substituted with an aspartic acid,
   (e) a tyrosine at position 209 substituted with a leucine,
   (f) a tyrosine at position 214 substituted with a threonine,
   (g) a lysine at position 235 substituted with a leucine,
   (h) a lysine at position 235 substituted with an arginine,
   (i) a lysine at position 237 substituted with an arginine,
   (j) a lysine at position 251 substituted with a glutamic acid, and
   (k) a lysine at position 251 substituted with an asparagine, wherein the mutation recited in claim 1 and the mutation described herein are at different positions of the subtilisin.

17. The modified subtilisin according to claim 16, comprising the following set of mutations in the amino acid sequence of the subtilisin: H17Q+K27R+H39S.

18. The modified subtilisin according to claim 16, comprising the following set of mutations in the amino acid sequence of the subtilisin: E54D+Y91F+K94R.

19. The modified subtilisin according to claim 16, comprising the following set of mutations in the amino acid sequence of the subtilisin: E54D+Y91F+K94R+H120D.

20. The modified subtilisin according to claim 16, comprising the following set of mutations in the amino acid sequence of the subtilisin: E54D+Y91F+K94R+H120N.

21. The modified subtilisin according to claim 16, comprising the following set of mutations in the amino acid sequence of the subtilisin: Y167F+Y171V+Y192F+Y209F+Y214T.

22. The modified subtilisin according to claim 16, comprising the following set of mutations in the amino acid sequence of the subtilisin: K235L+K237R+K251E+Y263F.

23. The modified subtilisin according to claim 16, comprising the following set of mutations in the amino acid sequence of the subtilisin: K235L+K237R+K251N+Y263F.

24. The modified subtilisin according to claim 16, comprising the following set of mutations in the amino acid sequence of the subtilisin: H226S+K235L+K237R+K251N+Y263F.

25. The modified subtilisin according to claim 16, comprising the following set of mutations in the amino acid sequence of the subtilisin: H226S+K235L+K237R+K251E+Y263F.

26. The modified subtilisin according to claim 16, comprising the following set of mutations in the amino acid sequence of the subtilisin: K235R+K237R+K251E+Y263F.

27. The modified subtilisin according to claim 16, comprising the following set of mutations in the amino acid sequence of the subtilisin: K235R+K237R+K251N+Y263F.

28. The modified subtilisin according to claim 16, comprising the following set of mutations in the amino acid sequence of the subtilisin: H226 +K235R+K237R+K251N+Y263F.

29. The modified subtilisin according to claim 16, comprising the following set of mutations in the amino acid sequence of the subtilisin: H226S+K235R+K237R+K251E+Y263F.

30. The modified subtilisin according to claim 18, comprising the following set of mutations in the amino acid sequence of the subtilisin: K27R+E54D+Y91F+K94R+ Y167F+Y171V+Y192F+Y209F+Y214T+K235L+K237R+ K251E+Y263F.

31. The modified subtilisin according to claim 17, comprising the following set of mutations in the amino acid sequence of the subtilisin: H17Q+K27R+H39S+E54D+ Y91F+K94R+H120D+Y167:F+Y171V+Y192F+Y209F+ Y214T+H226S+K235L+K237R+K251N+Y263F.

32. The modified subtilisin according to claim 17, comprising the following set of mutations in the amino acid sequence of the subtilisin: H17Q+K27R+H39S+E54D+ Y91F+K94R+H120N+Y167F+Y171V+Y192F+Y209F+ Y214T+H226S+K235L+K237R+K251E+Y263F.

33. The modified subtilisin according to claim 17, comprising the following set of mutations in the amino acid sequence of the subtilisin: H17Q+K27R+H39S+E54D+ Y91F+K94R+H120N+Y167F+Y171V+Y192F+Y209F+ Y214T+H226S+K235L+K237R+K251N+Y263F.

34. The modified subtilisin according to claim 17, comprising the following set of mutations in the amino acid sequence of the subtilisin: H17Q+K27R+H39S+E54D+ Y91F+K94R+H120D+Y167F+Y171V+Y192F+Y209F+ Y214T+H226S+K235L+K237R+K251E+Y263F.

35. The modified subtilisin according to claim 18, comprising the following set of mutations in the amino acid sequence of the subtilisin: K27R+E54D+Y91F+K94R+ Y167F+Y171V+Y192F+Y209F+Y214T+K235R+K237R+ K251E+Y263F.

36. The modified subtilisin according to claim 17, comprising the following set of mutations in the amino acid sequence of the subtilisin: H17Q+K27R+H39S+E54D+ Y91F+K94R+H120D+Y167F+Y171V+Y192F+Y209F+ Y214T+H226S+K235R+K237R+K251N+Y263F.

37. The modified subtilisin according to claim 17, comprising the following set of mutations in the amino acid sequence of the subtilisin: H17Q+K27R+H39S+E54D+ Y91F+K94R+H120N+Y167F+Y171V+Y192F+Y209F+ Y214T+H226S+K235R+K237R+K251E+Y263F.

38. The modified subtilisin according to claim 17, comprising the following set of mutations in the amino acid sequence of the subtilisin; H17Q+K27R+H39S+E54D+ Y91F+K94R+H120N+Y167F+Y171V+Y 192F+Y209F+ Y214T+H226S+K235R+K237R+K251N+Y263F.

39. The modified subtilisin according to claim 17, comprising the following set of mutations in the amino acid sequence of the subtilisin: H17Q+K27R+H39S+E54D+ Y91F+K94R+H120D+Y167F+Y171V+Y192F+Y209F+ Y214T+H226S+K235R+K237R+K251E+Y263F.

40. The modified subtilisin according to claim 18, comprising the following set of mutations in the amino acid sequence of the subtilisin: K27R+E54D+Y91F+K94R+ Y209F+Y214T+K235R+K237R+K251E+Y263F.

41. The modified subtilisin according to claim 35, further comprising mutations of the subtilisin of the histidine residues at positions 17, 39, 120 and 226 to neutral amino acid residues.

42. The modified subtilisin according to claim 1, wherein the subtilisin is selected from the group consisting of subtilisin BPN', subtilisin amylosacchariticus, subtilisin 168, subtilisin mesentericopeptidase, subtilisin Carlsberg, subtilisin DY, subtilisin 309, subtilisin 147, subtilisin thermitase, Bacillus PB92 protease, protease TW7, protease TW3, proteinase K and aqualysin.

43. The modified subtilisin according in claim 42, wherein the subtilisin is subtilisin 309.

44. The modified subtilisin according to claim 42, wherein the subtilisin is subtilisin 147.

45. A detergent composition comprising a surfactant and a modified subtilisin according to claim 1.

* * * * *

UNITED STATES PATENT AND TRADEMARK OFFICE
CERTIFICATE OF CORRECTION

PATENT NO.   : 5,482,849
DATED        : January 9, 1996
INVENTOR(S)  : Branner et al.

It is certified that error appears in the above-indentified patent and that said Letters Patent is hereby corrected as shown below:

Delete Claim 45 at Col. 28, lines 33-34.

Signed and Sealed this

Twenty-fifth Day of June, 1996

Attest:

BRUCE LEHMAN

*Attesting Officer*    *Commissioner of Patents and Trademarks*